(12) United States Patent
DiLeo et al.

(10) Patent No.: US 12,329,730 B2
(45) Date of Patent: Jun. 17, 2025

(54) THERMORESPONSIVE HYDROGEL CONTAINING POLYMER MICROPARTICLES FOR CONTROLLED DRUG DELIVERY

(71) Applicant: UNIVERSITY OF PITTSBURGH—OF THE COMMONWEALTH SYSTEM OF HIGHER EDUCATION, Pittsburgh, PA (US)

(72) Inventors: Morgan V. DiLeo, Mars, PA (US); Steven R. Little, Allison Park, PA (US); Joel S. Schuman, New York, NY (US)

(73) Assignee: University of Pittsburgh—Of the Commonweatlh System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/942,486

(22) Filed: Sep. 12, 2022

(65) Prior Publication Data

US 2023/0000802 A1    Jan. 5, 2023

Related U.S. Application Data

(62) Division of application No. 16/772,107, filed as application No. PCT/US2018/064707 on Dec. 10, 2018, now Pat. No. 11,484,515.
(Continued)

(51) Int. Cl.
*A61K 31/164* (2006.01)
*A61K 9/00* (2006.01)
(Continued)

(52) U.S. Cl.
CPC .......... *A61K 31/164* (2013.01); *A61K 9/0046* (2013.01); *A61K 9/06* (2013.01);
(Continued)

(58) Field of Classification Search
CPC .. A61K 31/164; A61K 31/167; A61K 31/496; A61K 31/546; A61K 31/573;
(Continued)

(56) References Cited

U.S. PATENT DOCUMENTS

| 7,220,431 B2 | 5/2007 | Sawchuk et al. |
| 2004/0101560 A1* | 5/2004 | Sawchuk ................ A61P 31/04 424/488 |

(Continued)

FOREIGN PATENT DOCUMENTS

| WO | WO 1990/001933 | 3/1990 |
| WO | WO 2004/045634 | 6/2004 |

(Continued)

OTHER PUBLICATIONS

Hoare et al., "Hydrogels in drug delivery: progress and challenges," *Polymer*, vol. 49, pp. 1993-2007, Jan. 19, 2008.
(Continued)

*Primary Examiner* — Sarah Pihonak
(74) *Attorney, Agent, or Firm* — Klarquist Sparkman, LLP

(57) ABSTRACT

Methods for treating an ear condition in a subject, comprising topically administering to the ear of the subject in need thereof a composition comprising: (i) an anti-infective agent-loaded biodegradable polymer microspheres; and (ii) a thermoresponsive hydrogel.

36 Claims, 7 Drawing Sheets

Related U.S. Application Data

(60) Provisional application No. 62/597,770, filed on Dec. 12, 2017.

(51) Int. Cl.

| | | |
|---|---|---|
| *A61K 9/06* | (2006.01) | |
| *A61K 9/16* | (2006.01) | |
| *A61K 31/167* | (2006.01) | |
| *A61K 31/496* | (2006.01) | |
| *A61K 45/06* | (2006.01) | |
| *A61P 27/16* | (2006.01) | |

(52) U.S. Cl.
CPC .......... *A61K 9/1647* (2013.01); *A61K 31/167* (2013.01); *A61K 31/496* (2013.01); *A61P 27/16* (2018.01); *A61K 45/06* (2013.01)

(58) Field of Classification Search
CPC ........ A61K 47/32; A61K 9/0046; A61K 9/06; A61K 9/1647; A61P 27/16; A61P 3/00
See application file for complete search history.

(56) References Cited

U.S. PATENT DOCUMENTS

| | | |
|---|---|---|
| 2009/0253809 A1 | 10/2009 | Gomurashvili et al. |
| 2013/0245569 A1 | 9/2013 | Jolly et al. |
| 2015/0374633 A1 | 12/2015 | Fedorchak et al. |
| 2017/0087248 A1 | 3/2017 | Kang-Mieler |
| 2017/0367981 A1 | 12/2017 | Little et al. |
| 2019/0099365 A1 | 4/2019 | Fedorchak et al. |

FOREIGN PATENT DOCUMENTS

| | | | |
|---|---|---|---|
| WO | WO 2006/002365 | 1/2006 | |
| WO | WO 2006/078924 | 7/2006 | |
| WO | WO-2006099325 A2 * | 9/2006 | ........... A61K 31/045 |
| WO | WO 2007/037874 | 4/2007 | |
| WO | WO 2009/132050 | 10/2009 | |
| WO | WO 2010/011609 | 1/2010 | |
| WO | WO 2014/138085 | 9/2014 | |

OTHER PUBLICATIONS

International Search Report and Written Opinion issued for International Application No. PCT/US2018/064707 on Mar. 10, 2019.

Khoo et al., "Formulations for trans-tympanic antibiotic delivery," *Biomaterials*, 34(4): 1281-1288, Jan. 2013.

Labib et al., "The long-term release of antibiotics from monolithic nonporous polymer implants for use as tympanostomy tubes," *Colloids Surf A Physicochem Eng Asp.* 254(1-3): 331-337, Feb. 5, 2010.

Mair et al., "Randomized clinical trial of a sustained-exposure ciprofloxacin for intratympanic injection during tympanostomy tube surgery," *Annals of Otology Rhinology & Laryngology*, 125(2): 105-114, Aug. 20, 2015.

Nakagawa et al., "Local drug delivery to the inner ear using biodegradable materials," *Therapeutic Delivery*, 2(6): 807-814, Jul. 12, 2011.

Piu et al., "OTO-104: A sustained-release dexamethasone hydrogel for the treatment of otic disorders," *Otology & Neurotology*, 32(1): 171-179, Jan. 2011.

Plontke et al., "Controlled release dexamethasone implants in the round window niche for salvage treatment of idiopathic sudden sensorineural hearing loss," *Otol. Neurotol.*, 35(7): 1168-1171, Aug. 2014.

Thomsen et al., "Preliminary results of a new delivery system for gentamicin to the inner ear in patients with Meniere's disease," *Eur Arch Otorhinolaryngol*, vol. 257, pp. 362-365, Aug. 2000.

U.S. Appl. No. 16/764,285, filed May 14, 2020.

Wang et al., "OTO-201: Nonclinical assessment of a sustained-release ciprofloxacin hydrogel for the treatment of otitis media," *Otology & Neurotology*, 35(3): 459-469, Mar. 2014.

Yang et al., "Treatment of otitis media by transtympanic delivery of antibiotics," *Sci. Transl. Med.*, 8(356): 1-22, Sep. 27, 2017.

* cited by examiner

THERMORESPONSIVE HYDROGEL CONTAINING POLYMER MICROPARTICLES FOR CONTROLLED DRUG DELIVERY

CROSS REFERENCE TO RELATED APPLICATIONS

This application is a divisional of U.S. application Ser. No. 16/772,107, filed Jun. 11, 2020, which is the U.S. National Stage of International Application No. PCT/US2018/064707, filed Dec. 10, 2018, which was published in English under PCT Article 21(2), which in turn claims the benefit of U.S. Provisional Application No. 62/597,770, filed Dec. 12, 2017, which is incorporated by reference herein in its entirety.

BACKGROUND

Acute otitis media (AOM), characterized by middle ear inflammation, acute onset, and duration of illness ranging from several days to two weeks, is the main indication for pediatric antibiotic prescription in the United States. In fact, over 25% of antibiotic prescription is for treating AOM. Recurrent AOM can develop into chronic otitis media, which requires further intervention such as the surgical placement of tympanostomy tubes for ventilation and drainage.

Oral antibiotics remain the standard of care, although such treatment is recognized as impractical due to the risks of systemic side effects and antibiotic resistance. Though less frequently prescribed for AOM, topical ear drops are also problematic, with less than 10% of the applied drug reaching the middle ear. For example, Cetraxal (0.2% ciprofloxacin), is delivered in quantities of 1-2 mg/day (Cetraxal product insert). The minimum inhibitory concentration (MIC) of ciprofloxacin is 2 µg/mL (Jacobs et al., Susceptibilities of *Streptococcus pneumoniae* and *Haemophilus influenzae* to 10 Oral Antimicrobial Agents Based on Pharmacodynamic Parameters: 1997 U.S. Surveillance Study Susceptibilities of *Streptococcus pneumoniae* and *Haemophilus influenzae* to 10 Ora. Antimicrobial agents and chemotherapy. 1999; 43(8):1901-8) with middle ear space of approximately 200 µL, yielding 0.4 µg/day necessary to clear infection. Thus, the current treatment delivers 500-1000 times excess drug, which can contribute to side effects and antibiotic resistance much like their oral counterparts. An ideal controlled release system would deliver an amount closer to the MIC of antibiotic to the middle ear.

Accordingly, research has focused on expanding and improving topical antibiotic treatment to address the aforementioned shortcomings. Studies by Otonomy, Inc. have shown success in releasing drugs from hydrogel vehicles placed either via intratympanic injection or during tympanostomy surgery (Mair et al., Randomized Clinical Trial of a Sustained-Exposure Ciprofloxacin for Intratympanic Injection During Tympanostomy Tube Surgery. Annals of Otology, Rhinology & Laryngology. 2015. doi: 10.1177/0003489415599001; PMCID: PMC4707869; Wang et al., OTO-201: nonclinical assessment of a sustained-release ciprofloxacin hydrogel for the treatment of otitis media. Otology & neurotology: official publication of the American Otological Society, American Neurotology Society [and] European Academy of Otology and Neurotology. 2014; 35(3):459-69; and Piu et al, OTO-104: a sustained-release dexamethasone hydrogel for the treatment of otic disorders. Otology & neurotology: official publication of the American Otological Society, American Neurotology Society [and] European Academy of Otology and Neurotology. 2011; 32(1):171-9). Some studies have included the use of degradable microspheres (MS) to further control drug release. While sustained release and efficacy in clearing infection and inflammation were observed from 2 weeks to 3 months, these systems require invasive procedures. Further, the gel cannot be retrieved from the middle ear and degradation products may cause long-term adverse effects.

Topical controlled release systems have also been investigated to improve AOM treatment, including ciprofloxacin-loaded hydrogels augmented by combinations of 3 different chemical permeation enhancers (CPEs), which resulted in transtympanic permeation (Khoo et al., Formulations for trans-tympanic antibiotic delivery. Biomaterials. 2013; 34(4):1281-8; and Yang et al, Treatment of otitis media by transtympanic delivery of antibiotics. Science translational medicine. 2016; 8(356):356ra120-356ra120). However, CPEs carry a risk of toxic side effects and have been shown to be cytotoxic during the preclinical validation of this system, with only 20% keratinocyte viability after 3 days. Further, recent studies suggest that outcomes may be improved when antibiotic treatment lasts 10 or more days, currently unachievable by these hydrogel-only systems. Achieving this duration of drug release typically requires a secondary controlled release vehicle such as hydrolytically degraded polymer microspheres (Hoare et al., Hydrogels in drug delivery: Progress and challenges. Polymer. 2008; 49(8):1993-2007).

SUMMARY

Disclosed herein are methods for treating an ear condition in a subject, comprising topically administering to the ear of the subject in need thereof a composition comprising: (i) anti-infective agent-loaded biodegradable polymer microparticles; and (ii) a thermoresponsive hydrogel.

Also disclosed herein are compositions comprising: (i) anti-infective agent-loaded biodegradable polymer microparticles; and (ii) a thermoresponsive hydrogel, wherein the hydrogel also includes an anesthetic, an anti-inflammatory, an antiseptic, or a combination thereof.

Further disclosed herein is a dual drug delivery system for delivery to the middle ear for treating acute otitis media comprising antibiotic-loaded biodegradable polymer microspheres delivered via a non-degradable thermoresponsive hydrogel matrix impregnated with lidocaine.

The foregoing will become more apparent from the following detailed description, which proceeds with reference to the accompanying figures.

DETAILED DESCRIPTION

Terminology

Figure 1C:
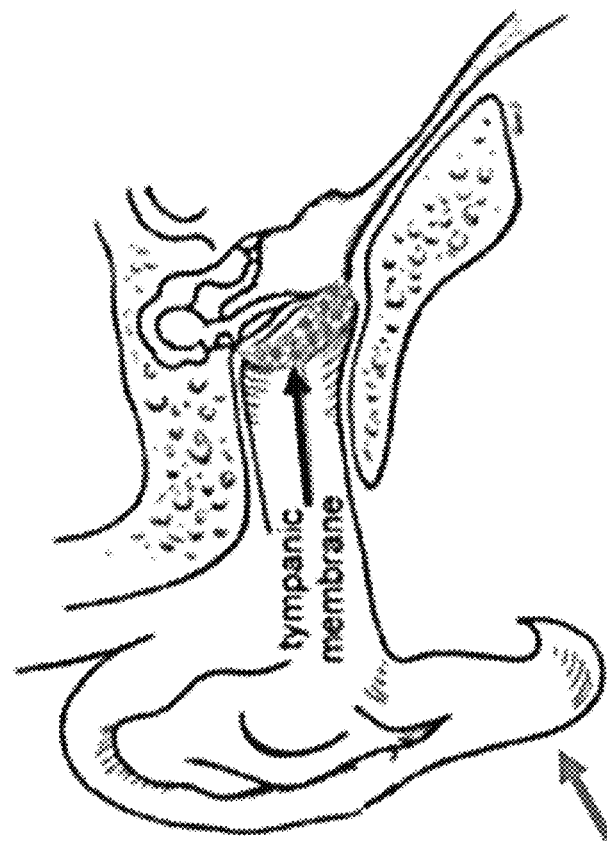
FIGS. 1A-1C show a schematic showing the use of a hydrogel drop containing biodegradable polymer microparticles that depicts topical administration (A), liquid-to-gel transition (B), and (C) antibiotic/anesthetic release over a period of days (e.g., 14 days).

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of an agent disclosed herein with at least one other therapeutic or diagnostic agent within the same general time period, and typically refers to administration at the same exact moment in time.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range. In certain embodiments, the microparticles may have a volume average diameter of 200 nm to 30 μm. In certain embodiments, the microparticles may have a volume average diameter from about 1 to about 25 microns, preferably from about 10 to about 25 microns, more preferably from about 10 to about 20 microns. In one embodiment, the particles have a volume average diameter from about 1 to about 10 microns, preferably from about 1 to about 5 microns, more preferably from about 2 to about 5 microns. As used herein, the microparticle encompasses microspheres, microcapsules, microparticles, microrods, nanorods, nanoparticles, or nanospheres unless specified otherwise. A microparticle may be of composite construction and is not necessarily a pure substance; it may be spherical or any other shape.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat otitis media without causing significant negative or adverse side effects to the ear.

"Treatment" refers to a therapeutic intervention that ameliorates a sign or symptom of an abnormal physical condition caused by trauma, a disease, or a pathological condition, after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to an abnormal physical condition caused by trauma, a disease or a pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, improved physical condition, or by other parameters well known in the art that are specific to the particular disease. The phrase "treating a disease" refers to inhibiting the full development of a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Disclosed herein is a drug delivery system that includes agent-loaded polymer microparticles distributed (e.g., suspended) within a thermoresponsive hydrogel. Degradable polymer microparticles (e.g., microspheres) offer the ability to sustain delivery of a drug for an extended period of time from a single, localized dose, tunability for various drugs and dosing ranges, and consistent daily release of therapeutic concentrations. The system is a liquid drop uses a liquid drop that becomes a solid gel at body temperature, enabling it to be retained in the affected area in a way that traditional liquid drops cannot. For example, the drug delivery system may be instilled similar to standard ear drops. The liquid precursor will form a pliable, non-degradable gel on the tympanic membrane (TM). Additionally, the slow and steady release of an agent drug afforded by the polymer microparticles allows for penetration to the middle ear and therapeutic effect at lower concentrations than systemically administered agent (e.g., antibiotics). The methods disclosed herein provide for transporting a therapeutically effective agent (e.g., an antibiotic) across the tympanic membrane (TM). All of this can be achieved without the use of harmful chemical permeation enhancers. Additionally, the drops could be administered in the clinic by a physician and removed upon routine follow-up so that patients never need to fill a prescription or administer any drops—thus essentially eliminating patient compliance concerns.

In certain embodiments, the hydrogel may also include a second agent (i.e., a therapeutic or diagnostic agent) that is different than the agent loaded in the polymer microparticles. The second agent may, or may not, also be encapsulated in a microparticle. In certain embodiments, the second agent is not encapsulated in a microparticle, but rather is freely dispersed within the hydrogel. Thus, the system disclosed herein can simultaneously deliver multiple drugs.

In particular embodiments, the system enable co-delivery of anesthesia to treat pain associated with otitis media while avoiding direct delivery of high levels of anesthesia to the middle ear that can result in nausea and dizziness. Controlled anesthetic delivery could also help with the primary goal of minimizing the administered dose of antibiotic, as lidocaine and benzocaine, common otic anesthetics, have both been shown to have antimicrobial effects. Synergism between anesthetic and an anti-infective agent (e.g., an antibiotic) being delivered could theoretically provide pain relief and long-lasting treatment of infection using significantly lower drug concentrations.

In certain embodiments, the drug delivery system will require only a single drop for the duration of treatment and will provide therapeutic levels of an anti-infective agent (e.g., an antibiotic) and anesthetic to the target area in a controlled and safe manner. The topical controlled release system for otitis media that is disclosed herein may provide continuous drug presentation at the tympanic membrane (TM), and simultaneous pain relief. Patient compliance may be dramatically improved, as only a single, clinician-administered drop will be needed for treatment. Side effects may be mitigated due to treatment localization to the middle ear and minimization of applied drug. Simple removal of the non-degradable hydrogel via irrigation may further reduce long-term adverse side effects due to lingering material or degradation products.

The systems disclosed herein provide at least one, and preferably all, of the following advantages:

Longer and more consistent duration of release than simple gel+drug systems;

Eliminate need for cytotoxic CPEs while providing dual pain relief and infection control; and/or.

Simple, non-invasive administration and removal, leaving no material or byproducts behind.

Figure 1A:
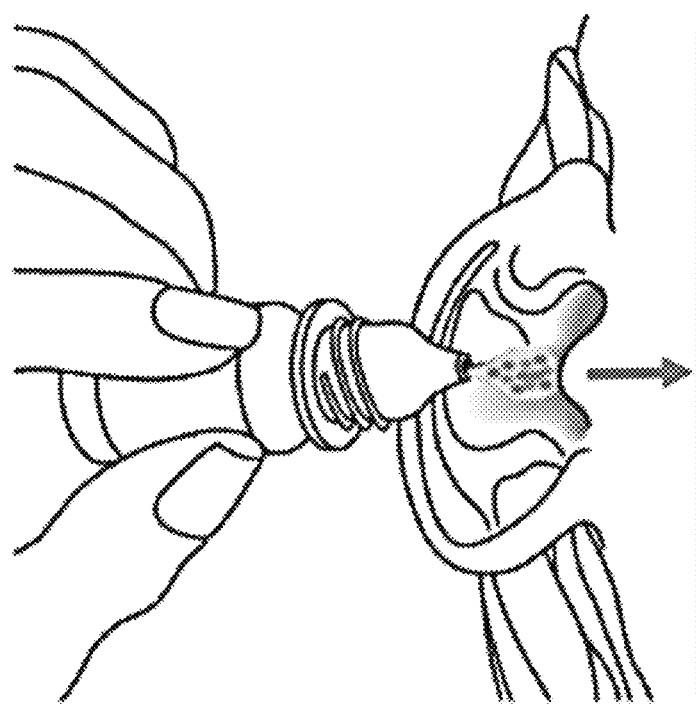
Figure 1B:
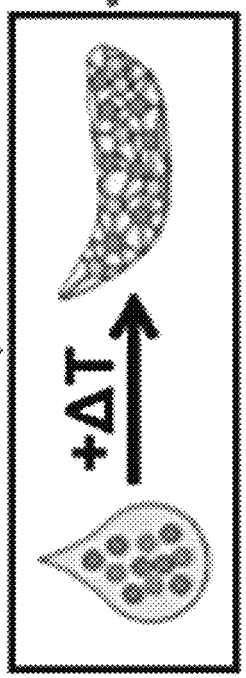

In certain embodiments, there is disclosed a dual drug delivery system to the middle ear for the treatment of acute otitis media through antibiotic-loaded biodegradable polymer microspheres (MS) delivered via a non-degradable thermoresponsive hydrogel matrix impregnated with lidocaine. The drug delivery composition may be instilled similar to standard ear. The liquid precursor will form a pliable, non-degradable gel on the TM that provides an immediate release of lidocaine, with prolonged release of ciprofloxacin at a near-constant rate as the MS degrade (see FIG. 1). The gel drop can then be flushed out with saline at the end of the dosing period, unlike degradable materials that remain well beyond the treatment window. This would help to address concerns about retrieval or long-term effects on hearing or biocompatibility.

Table 1 below shows examples of properties of certain embodiments of the thermoresponsive hydrogel.

| Property | Range | Rationale |
|---|---|---|
| Lidocaine release | 20-50 mg/ml for 1 day | Therapeutic effect |
| LCST | 33-35° C. | Sufficiently > room temp., <body temp. |
| Degradation | Negligible over 28 d | Intended for manual removal, not biodegradation |
| Swelling ratio | 5-10 | Rheological properties (instillation) and opacity (visualization) |

The gel is a thermoresponsive hydrogel that responds to external stimulus (e.g., physiological conditions) such as changes in temperature. In certain embodiments, the thermoresponsive hydrogel has a lower critical solution temperature (LCST) below body temperature. The thermoresponsive hydrogel remains fluid below physiological temperature (e.g., 37° C. for humans) or at or below room temperature (e.g., 25° C.), solidify (into a hydrogel) at physiological temperature, and are biocompatible. For example, the thermoresponsive hydrogel may be a clear liquid at a temperature below 33-35° C., particularly 34° C., which reversibly solidifies into a gelled composition at a temperature above 33-35° C., particularly 34° C. Generally, the LCST-based phase transition occurs upon warming in situ as a result of entropically-driven dehydration of polymer components, leading to polymer collapse. Various naturally derived and synthetic polymers exhibiting this behavior may be utilized.

Natural polymers include elastin-like peptides and polysaccharides derivatives, while notable synthetic polymers include those based on poly(n-isopropyl acrylamide) (PNIPAAm), poly(N,N-dimethylacrylamide-co-N-phenylacrylamide), poly(glycidyl methacrylate-co-N-isopropylacrylamide), poly(ethylene oxide)-b-poly(propylene oxide)-b-poly (ethylene oxide), poly(ethylene glycol)-polyester copolymer, and amphiphilic block copolymers. The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to about 2 upon the hydrophobic collapse above the LCST (32-34° C.). In certain embodiments, the amphiphilic block copolymer comprises a hydrophilic component selected from poly(dimethylsiloxane), poly ethylene oxide (PEO), poly vinyl alcohol (PVA), poly glycolic acid (PGA), poly (N-isopropylacrylamide), poly(acrylic acid) (PAA), poly vinyl pyrrolidone (PVP) or mixtures thereof, and a hydrophobic component selected from polypropylene oxide (PPO), poly (lactic acid) (PLA), poly (lactic acid co glycolic acid) (PLGA), poly (β-benzoyl L-aspartate) (PBLA), poly (γ-benzyl-L-glutamate) (PBLG), poly (aspartic acid), poly (L-lysine), poly(spermine), poly (caprolactone) or mixtures thereof. Examples of such amphiphilic block copolymers include (PEO)(PPO)(PEO) block copolymers (PEO/PPO), and poly (lactic acid co glycolic acid) block copolymers (PLGA), such as (PEO)(PLGA)(PEO) block copolymers.

In certain embodiments, the gel is non-biodegradable. Illustrative non-biodegradable thermoresponsive gels include PNIPAAm or a copolymer of n-isopropylacrylamide and at least one acrylic and/or methacrylic monomer. In certain embodiments, the Mw of the thermoresponsive hydrogel may be 5,000-20,000,000 Da. In certain embodiments, the mol % for the n-isopropylacrylamide monomer in the copolymerization reaction may be 70-95 mol %. Illustrative acrylic monomers include an acrylate such as an alkyl acrylate (e.g., methyl acrylate, ethyl acrylate, butyl acrylate or 2-ethylhexyl acrylate); an acrylamide; or an acrylic acid or salt (e.g., 2-ethylacrylic acid, 2-propylacrylic acid, N-acryloxysuccinimide). Illustrative methacrylic monomers include a methacrylate (e.g., 2-hydroxymethacrylate, hydroxyethyl methacrylate, butyl methacrylate, methyl ether methacrylate or methyl methacrylate); a methacrylamide; or a methacrylic acid or salt. In certain embodiments, the acrylate monomer or methacrylate monomer may be modified with poly(ethylene glycol) to provide a co-poly(ethylene glycol) acrylate or co-poly(ethylene glycol) methacrylate prior to reaction with the n-isopropylacrylamide monomer. In certain embodiments, the amount of PEG may range from 0.1-5% relative to the acrylate or methacrylate.

The gel may be made from a combination or mixture of any of the polymers disclosed herein.

The base precursor (e.g., a prepolymer, oligomer and/or monomer) for the gel, cross linkers, and initiators are mixed together and allowed to polymerize for a predefined period of time (from 1 h to 24 h typically) to form the gel. The gel may then be lyophilized prior to washing or the synthesized gel may be washed directly to remove any excess initiator or unreacted materials. The gel at this stage is a suspension/dispersion/emulsion or a lyophilized solid to which water may be added to reach the desired water content at room temperature until it is ready for use.

The agent for encapsulation in the microparticles may be a therapeutic agent such as, for example, an anti-infective agent (e.g., antiviral agent, an antibiotic agent or an antifungal agent). Illustrative anti-infective agents include quinolones (e.g., ofloxacin, ciprofloxacin, finafloxacin), aminoglycosides (e.g., neomycin, gentamicin, tobramycin), cephalosporins (e.g., ceftriaxone), tolnaftate, nystatin, clotrimazole, miconazole, or a combination thereof. In certain embodiments, ciprofloxacin is encapsulated in microparticles. Ciprofloxacin is a fluoroquinolone that affects most of the microorganisms responsible for OM, and is in fact the only antibiotic that treats *Pseudomonas*-based OM.

The second agent for inclusion in the delivery systems disclosed herein may be at least one other therapeutic agent. Illustrative therapeutic agents include an anesthetic, an anti-inflammatory, an antiseptic, or a combination thereof. Illustrative anesthetics include lidocaine, benzocaine, or a combination thereof. Illustrative anti-inflammatories include dexamethasone, hydrocortisone, or a combination thereof. Illustrative antiseptics include gentian violet, cersylate, mercurochrome, chloramphenicol, polymyxin, neomycin, or a combination thereof. The second agent may be dissolved in the water phase of the gel if the second agent is hydrophilic. The second agent may be suspended in the gel if the second agent is hydrophobic.

In certain embodiments the microparticle-encapsulated agent is ciprofloxacin and second agent is dexamethasone.

In certain embodiments, an acid (e.g., acetic acid) may be added to gel and/or microparticle, or co-administered with the gel/microparticle system for maintaining and/or restoring the proper pH of the ear canal.

If desired, the agent and/or agent-loaded microparticles can be added in, before, after, or during the polymerization of the gel to form a suspension of agent or solid microparticles in gel. In certain embodiments, adding microparticles in, before or during polymerization results in a slighter faster initial drug release rate.

The agent may be provided in the form of agent-loaded microparticles. The polymers for the microparticle may be bioerodible polymers so long as they are biocompatible. Preferred bio-erodible polymers are polyhydroxyacids such as polylactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpyrrolidone, alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

A preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, acid-terminated, referred to as 502H); poly(D,L-lactic-co-glycolic acid) (PLGA, 50:50 lactic acid to glycolic acid ratio, $M_n$=25 kDa, acid-terminated, referred to as 503H); poly(D,L-lactic-co-glycolic acid) (PLGA, 50:50 lactic acid to glycolic acid ratio, $M_n$=30 kDa, acid-terminated, referred to as 504H); poly(D, L-lactic-co-glycolic acid) (PLGA, 50:50 lactic acid to glycolic acid ratio, $M_n$=35 kDa, ester-terminated, referred to as 504); and poly(D,L-lactic-co-glycolic acid) (PLGA, 75:25 lactic acid to glycolic acid ratio, $M_n$=10 kDa, referred to as 752).

In certain embodiments, the polymer is an ester-terminated PLGA.

In certain embodiments, the polymer is a polyethylene glycol-poly(lactic-co-glycolic acid) copolymer.

In certain embodiments, the polymer microparticles are biodegradable.

The amount of microparticles loaded into the hydrogel may vary. For example, there may be up to 10 mg, more particularly 1 to 5 mg microparticles per microliter hydrogel. In certain embodiments, the microparticles are homogeneously dispersed within the hydrogel. Optional components can be added that allow for easier visualization of the hydrogel/microparticle suspension such as sodium fluorescein or other fluorescent molecules such as FITC, rhodamine, or AlexaFluors or dyes such as titanium dioxide. The water content of the swollen hydrogel at room temperature may be 50-80%. The water content of the hydrogel after it gels in situ in the eye may be 1-10%.

In certain embodiments, the amount of agent loaded into the microparticles may from 1 ng to 1 mg, more particularly 1 to 100 µg, and most particularly, 20 to 30 µg agent per mg of microparticles. In certain specific embodiments, the amount of agent loaded into the microparticles is 25 to 30 µg agent per mg of microparticles.

The agent-loaded microparticles may be pore less or they may contain varying amounts of pores of varying sizes, typically controlled by adding NaCl during the synthesis process.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics. The agent-loaded microparticles may be made, for example, as disclosed in U.S. Patent Application Publication No. 2015-0374633.

In certain embodiments, the agent-loaded microparticle can provide for a controlled, sustained release of the encapsulated agent over an extended time period. For example, the sustained release may be over a period of at least one day, more particularly at least seven days or at least 21 days. In certain embodiments, the encapsulated agent is released for a period of up to seven days, more particularly 14 days. The agent release can be linear or non-linear (single or multiple burst release). In certain embodiments, the agent may be released without a burst effect. For example, the sustained release may exhibit a substantially linear rate of release of the therapeutic agent in vivo over a period of at least one day, more particularly at least seven days or at least 21 days. By substantially linear rate of release it is meant that the therapeutic agent is released at a rate that does not vary by more than about 20% over the desired period of time, more usually by not more than about 10%. In certain embodiments, the microparticle-encapsulated agent is sustainably released in an amount of 0.5 mg to 10 mg per day, more particularly 1 mg to 10 mg per day.

In certain embodiments, the agent release is dependent on degradation of the polymer microparticles. As the polymer chains break up, the agent can diffuse out of the initial polymer microparticle matrix where it will eventually reach the hydrogel matrix. At that point, the hydrogel may partially slow down release of the agent but diffusion through the hydrogel is significantly faster than degradation of the polymer. Thus the limiting factor in agent release is degradation of the polymer.

The microparticle disclosed herein may provide for controlled release of an agent. The term "controlled release" as used herein, refers to the escape of any attached or encapsulated factor at a predetermined rate. For example, a controlled release of an agent may occur resulting from the predicable biodegradation of a polymer particle (i.e., for example, an artificial antigen presenting cell). The rate of biodegradation may be predetermined by altering the polymer composition and/or ratios comprising the particle. Consequently, the controlled release may be short term or the controlled release may be long term.

The gel disclosed herein may provide for immediate, delayed, or sustained release of an agent. In certain embodiments, a second agent that is not encapsulated in a particle may be included in the gel. In such embodiments, the second agent release from the gel could be adjusted by modifying the degree of crosslinking. For example, the second agent may be released from the gel over a period of one hour to three days. In certain embodiments, the second agent is an anesthetic that is immediately released via a burst release (e.g, within one hour after administration). In certain embodiments, the second agent is sustainably released in an amount of 0.5 mg to 10 mg per day.

The gel or mixture of gel and microparticles disclosed herein may include an excipient component, such as effective amounts of buffering agents, or antioxidants to protect a drug (the therapeutic agent) from the effects of ionizing radiation during sterilization. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

The systems disclosed herein can be used for treating a variety of ear pathologies. Illustrative ear pathologies include acute or chronic otitis media, acute or chronic otitis externa, tympanic membrane perforation, otomycosis, stenosis, herpes zoster, or myringitis.

Certain embodiments are described below in the following numbered clauses:

1. A method for treating an ear condition in a subject, comprising topically administering to the ear of the subject in need thereof a composition comprising: (i) an anti-infective agent-loaded biodegradable polymer microspheres; and (ii) a thermoresponsive hydrogel.

2. The method of clause 1, wherein the anti-infective agent is selected from an antiviral agent, an antibiotic agent, an antifungal agent or a combination thereof.

3. The method of clause 1 wherein the anti-infective agent is selected from ofloxacin, ciprofloxacin, finafloxacin, neomycin, gentamicin, tobramycin, tolnaftate, nystatin, clotrimazole, miconazole, or a combination thereof.

4. The method of any one of clauses 1 to 3, wherein the ear condition is otitis media.

5. The method of clause 4, wherein the ear condition is acute otitis media.

6. The method of clause 4, wherein the ear condition is chronic otitis media.

7. The method of any one of clauses 1 to 3, wherein the ear condition is acute or chronic otitis media, acute or chronic otitis externa, tympanic membrane perforation, otomycosis, stenosis, herpes zoster, or myringitis.

8. The method of any one of clauses 1 to 7, wherein only a single drop of the composition is administered for the duration of treatment.

9. The method of any one of clauses 1 to 8, wherein the method provides for a sustained linear release rate of the anti-infective agent.

10. The method of any one of clauses 1 to 9, wherein the anti-infective agent is released at a rate of 1 mg to 10 mg per day.

11. The method of any one of clauses 1 to 10, wherein the anti-infective agent is released for up to 14 days after administration.

12. The method of any one of clauses 1 to 11, wherein the hydrogel also includes an anesthetic, an anti-inflammatory, an antiseptic, or a combination thereof.

13. The method of clause 12, wherein the anesthetic is lidocaine, benzocaine, or a combination thereof.

14. The method of clause 12, wherein the anti-inflammatory is dexamethasone, hydrocortisone, or a combination thereof.

15. The method of clause 12, wherein the antiseptic is gentian violet, cersylate, mercurochrome, chloramphenicol, polymyxin, neomycin, or a combination thereof.

16. The method of any one of clauses 1 to 12, wherein the anti-infective agent is ciprofloxacin and the hydrogel also includes dexamethasone.

17. The method of any one of clauses 1 to 16, further comprising co-administering an acid for maintaining and/or restoring the pH of the ear canal.

18. The method of clause 12, wherein the anesthetic, anti-inflammatory, or antiseptic is dissolved in an aqueous phase of the hydrogel.

19. The method of clause 12, wherein the anesthetic, anti-inflammatory, or antiseptic is suspended within the hydrogel.

20. The method of clause 12, wherein the anesthetic, anti-inflammatory, or antiseptic is immediately released.

21. The method of clause 12, wherein the anti-infective agent and the anesthetic, anti-inflammatory, or antiseptic are simultaneously released for at least partial amount of the time that the composition resides within the ear.

22. The method of any one of clauses 1 to 21, wherein the composition resides within the ear for at least seven days after administration.

23. The method of any one of clauses 1 to 21, further comprising removing the composition from the ear within 21 days after administration.

24. The method of clause 23, wherein removing the composition comprises irrigation of the ear with saline.

25. The method of any one of clauses 1 to 24, wherein the anti-infective agent comprises ciprofloxacin.

26. The method of any one of clauses 12 or 17 to 25, wherein the anesthetic comprises lidocaine.

27. The method of any one of clauses 1 to 26, wherein the composition does not include a chemical permeation enhancer.

28. A composition comprising: (i) an anti-infective agent-loaded biodegradable polymer microspheres; and (ii) a thermoresponsive hydrogel, wherein the hydrogel also includes an anesthetic, an anti-inflammatory, an antiseptic, or a combination thereof.

29. The composition of clause 28, wherein the anti-infective agent-loaded biodegradable polymer microspheres and the anesthetic, anti-inflammatory, or antiseptic are both distributed within the hydrogel.

30. The composition of clause 28, wherein the anti-infective agent is selected from an antiviral agent, an antibiotic agent, an antifungal agent or a combination thereof.

31. The composition of clause 30, wherein the anti-infective agent is selected from ofloxacin, ciprofloxacin, finafloxacin, neomycin, gentamicin, tobramycin, tolnaftate, nystatin, clotrimazole, miconazole, or a combination thereof.

32. The composition of clause 30, wherein the anti-infective agent comprises ciprofloxacin.

33. The composition of any one of clauses 30 to 32, wherein the anesthetic is lidocaine, benzocaine, or a combination thereof.

34. The composition of any one of clauses 30 to 32, wherein the anti-inflammatory is dexamethasone, hydrocortisone, or a combination thereof.

35. The composition of any one of clauses 30 to 32, wherein the antiseptic is gentian violet, cersylate, mercurochrome, chloramphenicol, polymyxin, neomycin, or a combination thereof.

36. The composition of any one of clauses 30 to 32, wherein the anesthetic comprises lidocaine.

37. The composition of any one of clauses 30 to 36, wherein the composition does not include a chemical permeation enhancer.

38. The composition of any one of clauses 30 to 37, wherein the polymer microparticles comprise polylactic-co-glycolic) acid.

39. The composition of any one of clauses 30 to 38, wherein the hydrogel comprises N-isopropylacrylamide.

40. A dual drug delivery system for delivery to the middle ear for treating acute otitis media comprising antibiotic-loaded biodegradable polymer microspheres delivered via a non-degradable thermoresponsive hydrogel matrix impregnated with lidocaine.

EXAMPLES

Ciprofloxacin-loaded microspheres were prepared using a double emulsion procedure. In brief, 200 mg polylactic-co-glycolic) acid (PLGA) (MW 24-38 kDa; viscosity 0.32-0.44 dL/g; Sigma Aldrich, St Louis, MO) were dissolved in 4 mL dichloromethane to which 250 µL, of 100 mg/mL ciprofloxacin in 1M acetic acid was added. The dissolved drug and polymer mixture were then sonicated for 10 s at 30% amplitude (EpiShear Probe Sonicator, Active Motif, Carlsbad, CA) followed by homogenization in 60 mL of 2% poly(vinyl alcohol) (PVA) (Polysciences, Warrington, PA) for 1 minute at 7000 rpm (Silverson L5M-A, East Longmeadow, MA). The resulting liquid-phase emulsion was added to 80 mL of 1% PVA and stirred at 600 rpm for 3 hours, resulting in precipitation of solid microspheres. Drug-loaded and blank microspheres, fabricated by substituting DI water for aqueous drug, were then washed 4 times by centrifugation, resuspended in DI water, flash frozen in liquid N2, and lyophilized for 24-48 hours (Speedvac Freezone, Labconco, Kansas City, MO).

Figure 2:
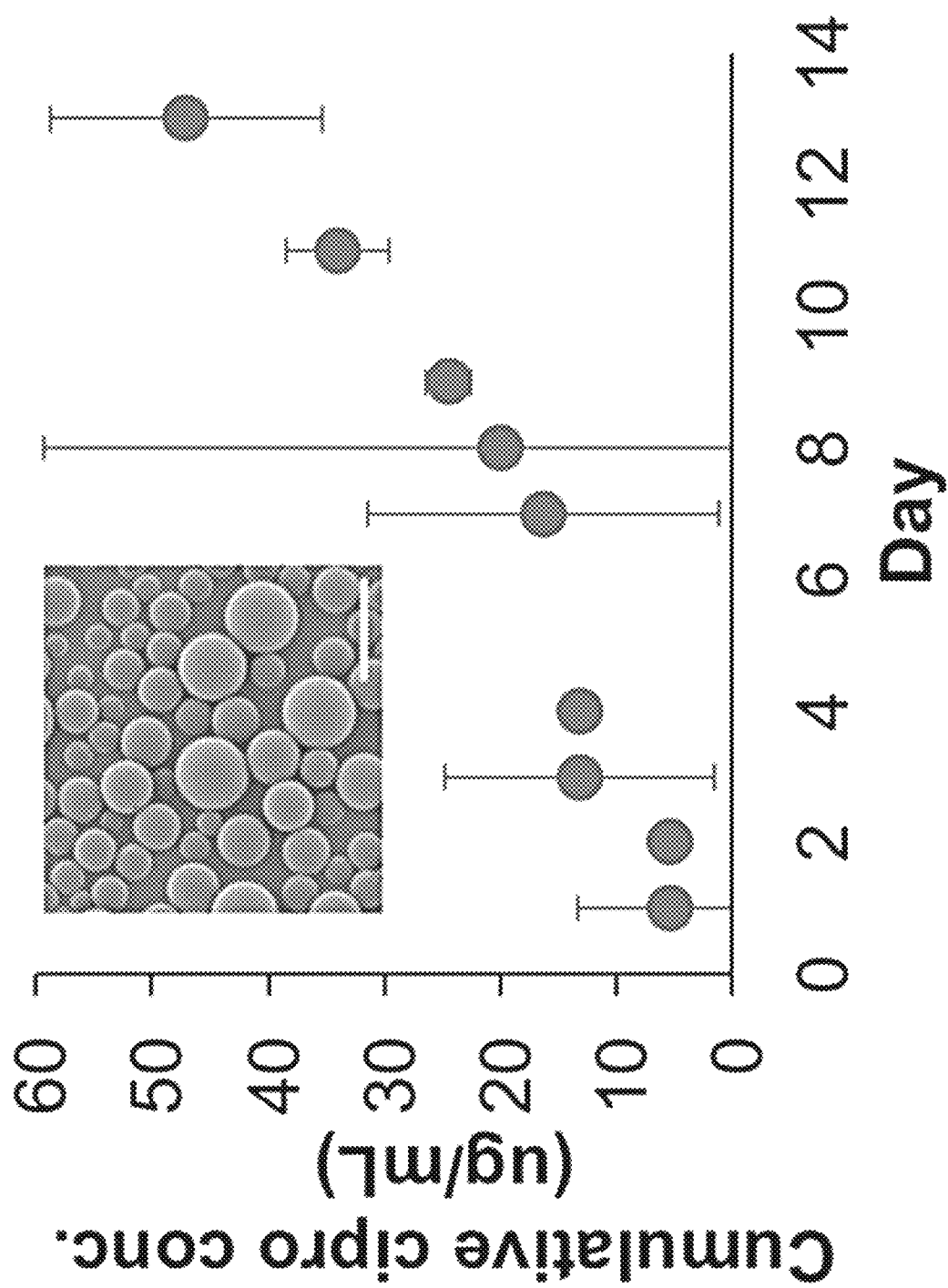
FIG. 2 is a graph showing cumulative ciprofloxacin release from a degradable microsphere (MS) formulation (inset, scale=10 µm).

Scanning electron microscopy (SEM) of ciprofloxacin-loaded PLGA microspheres shows a primarily poreless morphology and average diameter of approximately 10 µm (FIG. 2, inset). A standard curve for ciprofloxacin was determined, with a linear region observed for 1-9 µg/mL, containing the expected daily release of 4 µg/mL. Initial release studies show constant near-linear release of ciprofloxacin over 14 days (FIG. 2). We have separately confirmed that incorporation of ciprofloxacin-loaded MS into the thermoresponsive hydrogel does not affect its properties including phase transition temperature.

Ex Vivo Model Validation.

Figure 3:
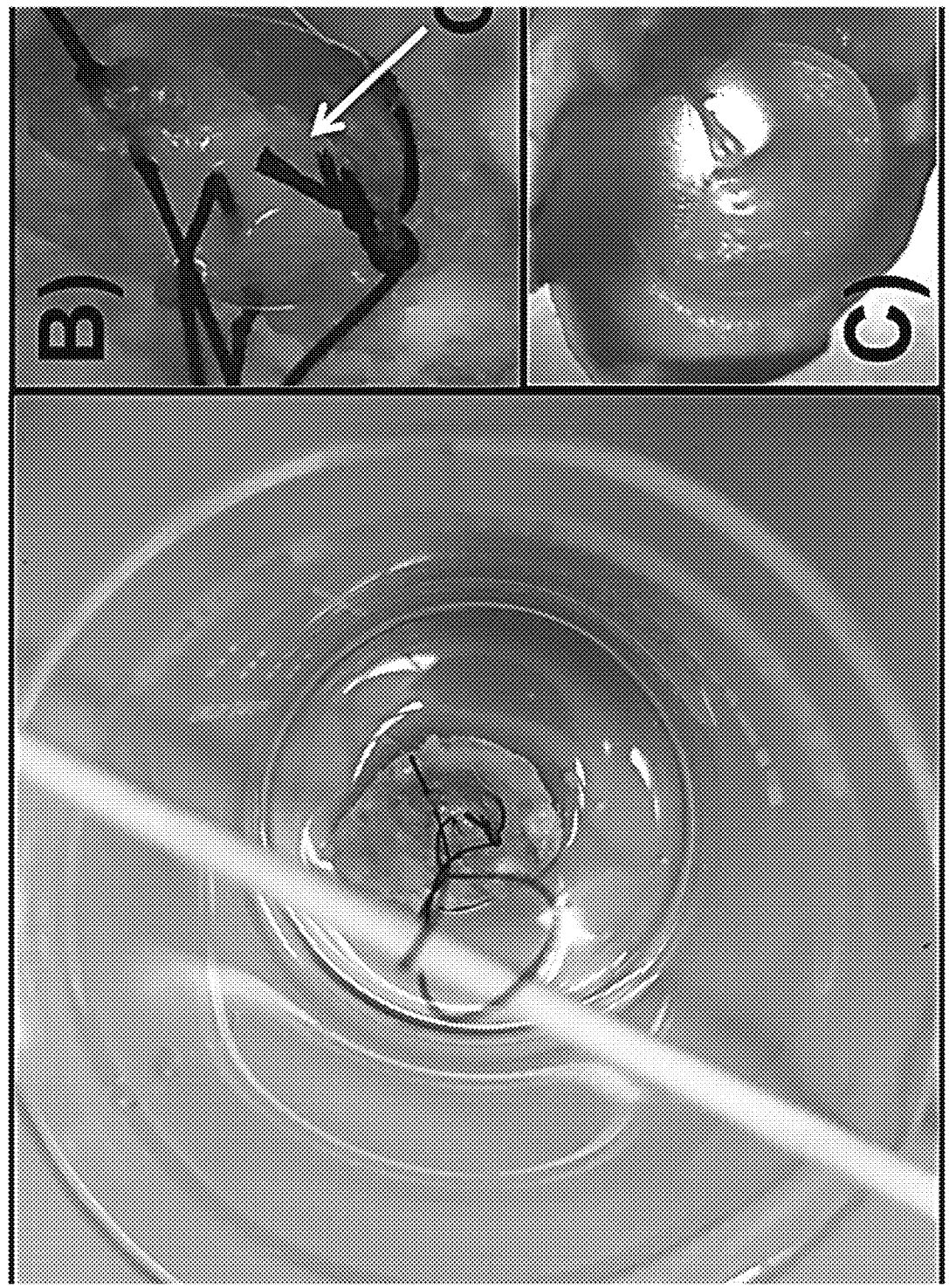
FIG. 3 shows an ex vivo experimental setup. (A) Top view, (B) application of gel/microsphere drop, (C) reverse view of intact tympanic membrane.
Figure 4:
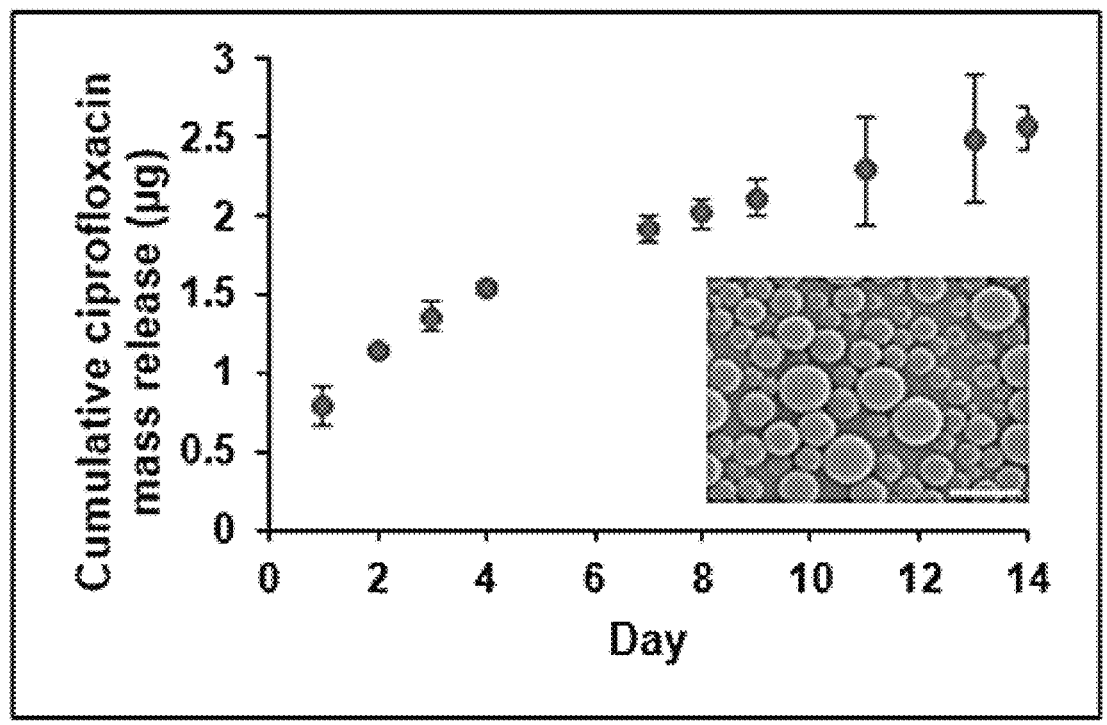
FIG. 4 is a graph showing in vitro release of ciprofloxacin from MS over 14 days. Inset: Scanning electron microscopy image of ciprofloxacin-loaded MS (scale bar=10 µm).
Figure 5:
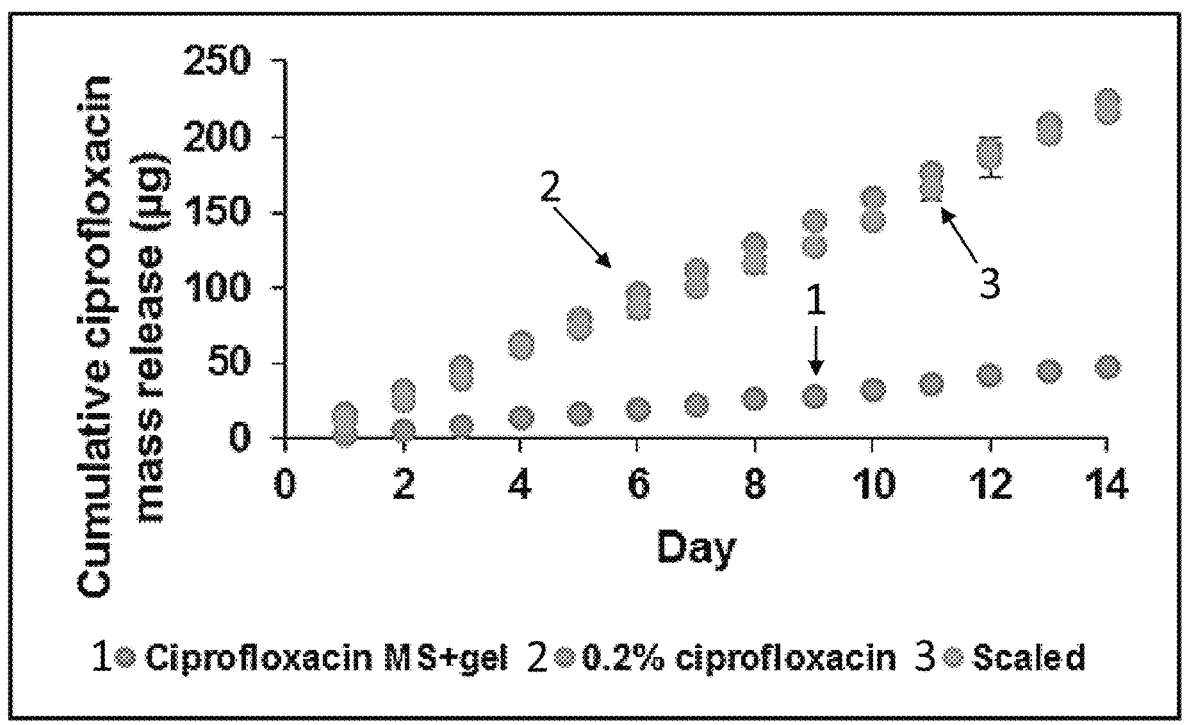
FIG. 5 is graph depicting ex vivo results showing transtympanic release from gel-MS system, standard topical drops (0.2% ciprofloxacin), and release scaled to human ear anatomy.
Figure 6:
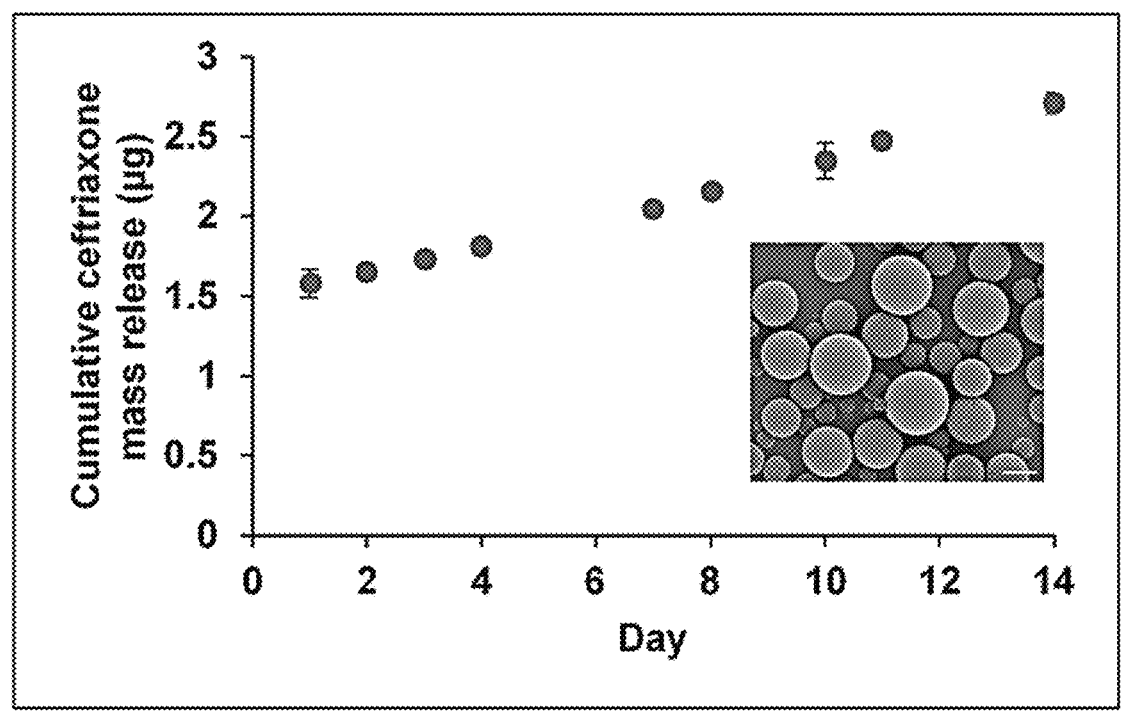
FIG. 6 is a graph depicting in vitro release of ceftriaxone from MS over 14 days. Inset: Scanning electron microscopy image of ceftriaxone-loaded MS (scale bar=10 μm).
Figure 7:
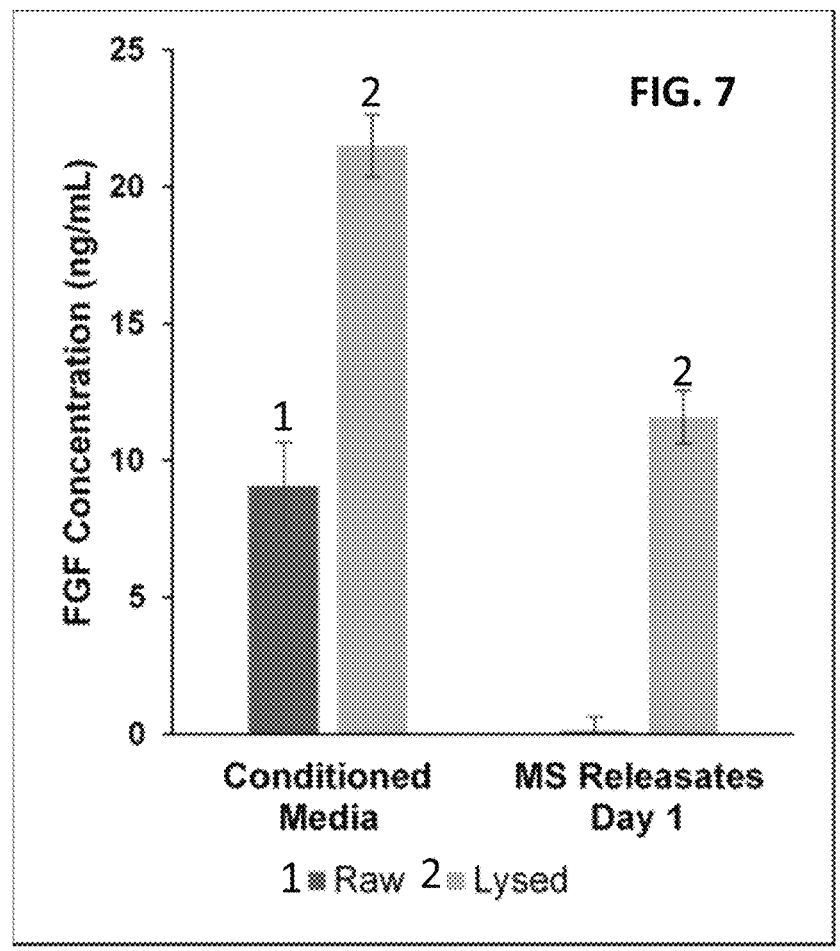
FIG. 7 is a graph depicting human adipose derived mesenchymal stem cell conditioned media and conditioned media-loaded microsphere day 1 releasates before and after lysis. Lysis confirms presence of growth factor, specifically FGF2, both free and encapsulated in extracellular vesicles.
Figure 8:
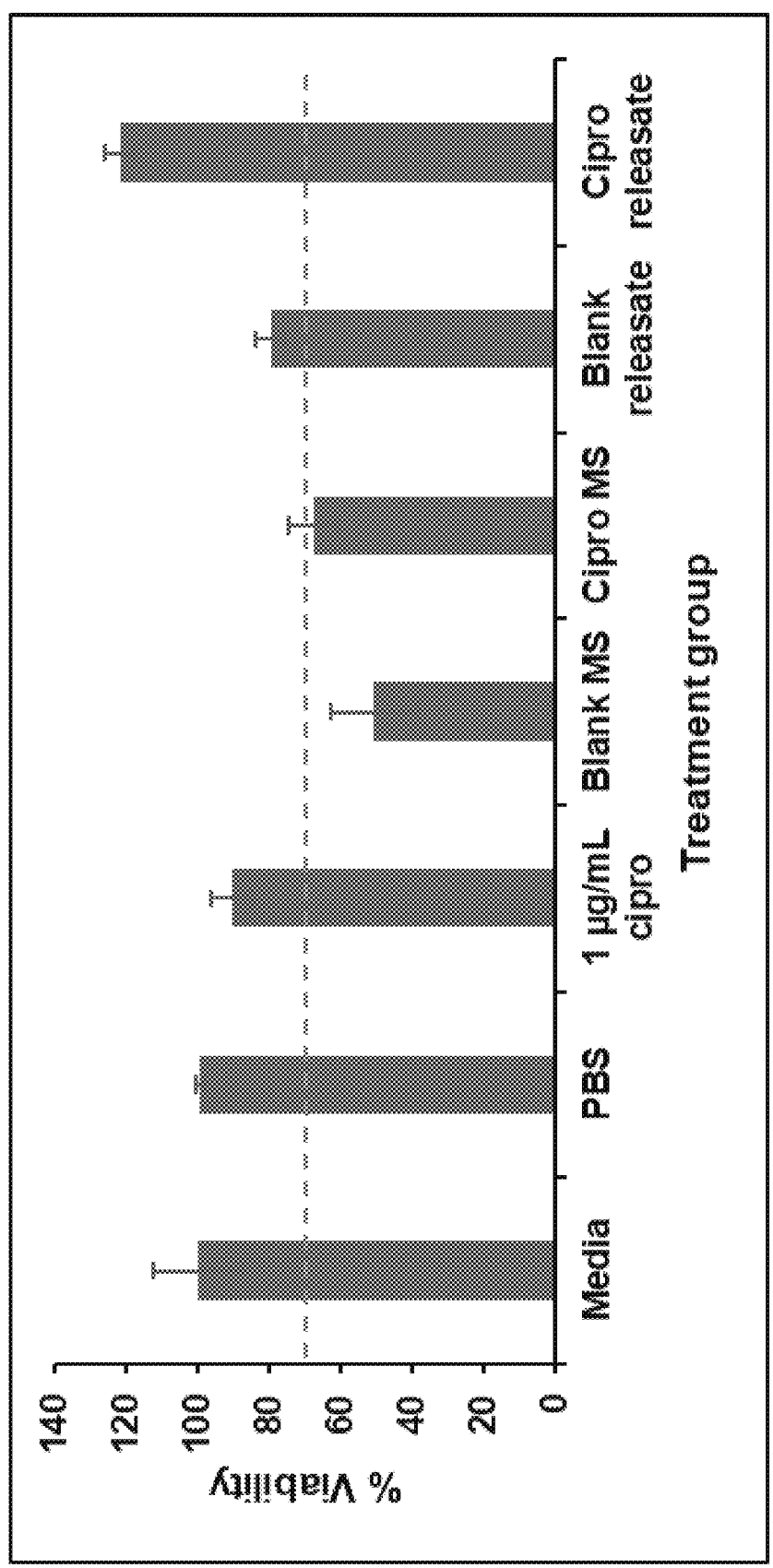
FIG. 8 is a graph depicting MTT cell viability assay shows acceptable levels of cytotoxicity due to application of microspheres and microsphere releasates to human dermal keratinocytes for 24 hours. Red dotted line indicates 70% viability, the minimum accepted by the FDA.
Figure 9:
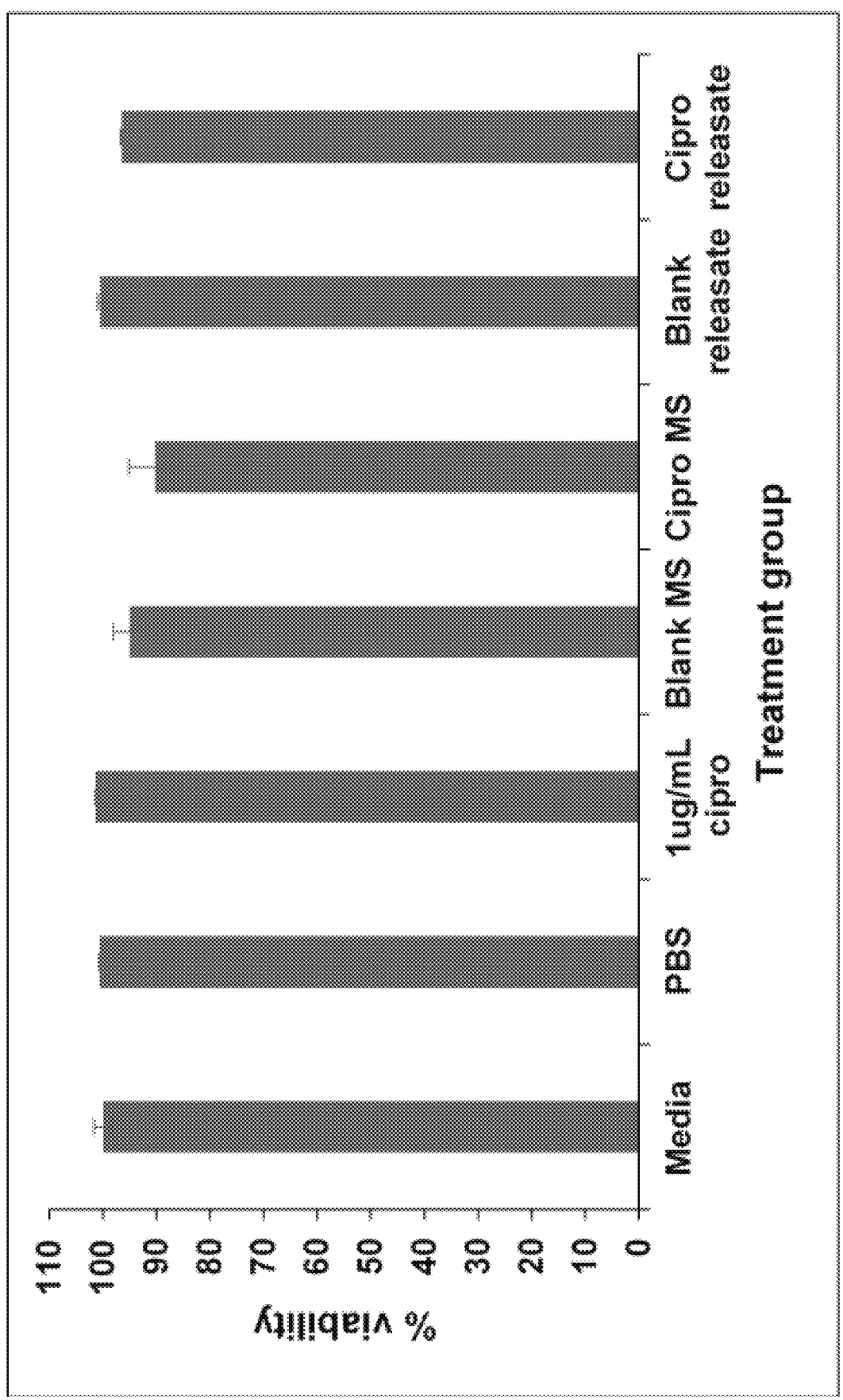
FIG. 9 is a graph depicting LIVE/DEAD cell viability assay shows acceptable levels of cytotoxicity due to application of microspheres and microsphere releasates to human dermal keratinocytes for 24 hours. Red dotted line indicates 70% viability, the minimum accepted by the FDA.

FIG. 3 demonstrates our ability to harvest tissue post-mortem from guinea pigs for ex vivo permeability studies. Ear canals and intact TMs can be removed without damage (FIG. 3).

Experimental Approach.

The base hydrogel may be prepared via free radical polymerization of N-isopropylacrylamide (NIPAAm) (Fisher Scientific, Waltham, MA) and poly(ethylene glycol) (MW~200 kDa; Sigma Aldrich, St Louis, MO), in the presence of ammonium persulfate (APS) and tetramethylethylenediamine. The gel precursor is refrigerated overnight and then washed 5 times in DI water at ~40° C. Lidocaine loading at a minimum of 5% total concentration will occur prior to polymerization, with no more than 50% by volume being occupied by aqueous lidocaine.

Lidocaine release from the gel will be measured by periodically collecting liquid supernatant from gel samples incubated at 37° C. Detection will be performed using a previously reported HPLC method validated for the range 20-1000 ng/ml. Each gel formulation will also undergo testing for degradation rate, swelling ratio, and lower critical solution temperature (LCST, the temperature at which gelation occurs), which have been well-characterized for the drug-free gel material. LCST will be determined via absorbance at 415 nm over incrementally increasing temperatures. Degradation rate will be determined by comparing mass of liquid gel at baseline and up to 14 days in the gel phase. Swelling ratio will be determined by comparing the dry and swollen weight of gel for multiple samples. Table 1 above shows the targeted criteria for the drug-loaded gel.

Refinements to the ciprofloxacin-loaded microsphere formulation will be directed to maintaining current properties when suspended in the lidocaine-loaded hydrogel and improving the linearity of release over the desired two-week time frame. In particular, linearity of ciprofloxacin release in days 0-7 will be optimized. Size, shape, porosity, and drug loading and release will be characterized for each set of MS prepared. Scanning electron microscopy (SEM) will be used to examine shape and morphology of both blank and drug-loaded MS (JEOL JSM 6335F, Peabody, MA). MS diameter will be determined by volume impedance measurements (Multisizer, Beckman Coulter, Brea, CA). To determine drug loading, 10 mg of blank and drug-loaded MS will be weighed out and rotated in an incubator at 37° C. for 1 hour after addition of 1 mL DMSO. Then, 5 mL of NaOH-SDS (0.05N NaOH, 5% SDS) will be added to each and rotated for an additional hour. UV/Vis absorbance measures will be taken at 246 nm (SoftMax Pro 5, Molecular Devices, Sunnyvale, CA) and regressed against the standard curve, validated from 1-10 ug/ml using 5:1 NaOH-SDS:DMSO.

In vitro drug release kinetics will be determined using known masses of MS suspended in phosphate buffered saline (PBS) and continuously rotated at 37° C. The supernatant will be removed via centrifugation every 24 hours for 14 days and replaced with fresh PBS. Drug concentration in the supernatant will be quantified via UV/Vis absorption at 246 nm, with background signal from blank MS subtracted from each measurement. Drug concentration will also be confirmed by measurement via high performance liquid chromatography (HPLC, Agilent Technologies 1220 Infinity LC) using the following settings: Kromasil C18 column (4.6 mm×150 mm, 3.5 μm particles; Sigma Aldrich, St Louis, MO), 10 μL injection volume, 80:20 acetonitrile:0.1% trifluoroacetic acid mobile phase, 1 mL/min flow rate, detection at 275 nm.

The MIC for ciprofloxacin is 0.4 μg/day and transtympanic permeability is estimated at 10%, therefore the target drug release is 4 ug/day.

For the full study, we will use 60 male Hartley guinea pigs, with 15 total ears in each of 7 test groups (Table 2 below).

TABLE 2

Ex vivo groups.

|  | Lido | Cipro |
|---|---|---|
| Gel/MS1 | − | − |
| Gel/MS2 | − | + |
| Gel/MS3 | + | − |
| Gel/MS4 | + | + |
| Control 1 | + | − |
| Control 2 | − | + |
| Control 3 | + | + |

There will be 5 time points used and n=3 ears per time point, with an additional 15% to account for unanticipated perforations or other issues in the TM (120 ears total). Each gel/MS drop will contain 10 mg of MS loaded into 100 μL, of hydrogel. Ear canals will be harvested humanely from guinea pigs post-mortem and TMs will be inspected visually via dissecting microscope to confirm lack of perforation. Each TM will be suspended in a beaker filled with 10 mL PBS, with the TM parallel to the bottom of the beaker and only the surface of the TM submerged in the PBS. The samples will be stored at 37° C. and 100 μL of gel/MS or 2 standard drops of will be added to the ear canal. Gel/MS samples will be aged separately in PBS at 37° C. in triplicate for either 1, 3, 7, 10, or 14 days and added to three freshly harvested ear canals each day to avoid concerns of tissue degradation over time. Samples will be taken from the receiving chamber and drug concentration measurements performed using the methods described above. This study will then be repeated for the Gel/MS Group 4 and Control Group 3 only using animals that have been inoculated with S. pneumoniae, according to the methods below, to determine the effect of inflammation on permeability. Thus the grand total of guinea pigs will be 78, as the disease model adds 30 more ears. Cytocompatibility will be determined both qualitatively via LIVE/DEAD staining and quantitatively using PrestoBlue cell viability reagent (ThermoFisher).

Preliminary In Vivo Determination of Safety and Synergistic Anti-Microbial Effects.

This tests the safety and effectiveness of the new drug release system in vivo, as demonstrated by clearance of infection and lack of irritation due to drop placement.

Guinea pigs are a standard and well-accepted model for middle and inner ear pharmacokinetics. Due to the guinea pigs' ear physiology, there is a large middle ear component and easy access to the cochlear structure, facilitating administration of drug to the middle ear. A power analysis was used to calculate required number of animals for statistically significant results based on a similar study that used n=5 per group (19) with power=0.8 and α=0.05 for control peak ciprofloxacin concentration=4.2 μg/mL and test peak ciprofloxacin concentration=39.1 μg/mL. This confirmed that n=5 animals per group will be sufficient, with a total of 25 animals required. Male Hartley guinea pigs will be randomly divided into the following groups listed in Table 2 above: Gel/MS 1, Gel/MS 2, Gel/MS 4, Control 2, and Control 3. We are foregoing the lidocaine only groups to focus on measurable efficacy and synergistic effects of both drugs. One ear of each animal will be inoculated with *S. pneumoniae*, the most common bacteria present in AOM, 24 hours prior to treatment via a transbullar injection of 0.15-0.2 mL of 2.6-4.5×10e7 CFU/mL (17). On Day 0, Gel/MS Groups will receive one gel/MS drop (blank or drug loaded). Control Groups will receive topical drops according to a typical dosing regimen of 2 drops daily for 7 days for ciprofloxacin and twice daily for 1 day for lidocaine. The duration of the study will be 14 days after instillation of gel/MS drop.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating an ear condition in a subject, comprising topically administering to the ear of the subject in need thereof a composition comprising (i) anti-infective agent-loaded biodegradable polymer microparticles distributed within a thermoresponsive hydrogel; and (ii) an anesthetic distributed within the thermoresponsive hydrogel, wherein the anesthetic is lidocaine, benzocaine, or a combination thereof, and wherein the anesthetic is immediately released.

2. The method of claim 1, wherein the anti-infective agent is selected from an antiviral agent, an antibiotic agent, an antifungal agent or a combination thereof.

3. The method of claim 1 wherein the anti-infective agent is selected from ofloxacin, ciprofloxacin, finafloxacin, neomycin, gentamicin, tobramycin, tolnaftate, nystatin, clotrimazole, miconazole, or a combination thereof.

4. The method of claim 1, wherein the ear condition is otitis media.

5. The method of claim 4, wherein the ear condition is acute otitis media.

6. The method of claim 4, wherein the ear condition is chronic otitis media.

7. The method of claim 1, wherein the ear condition is acute or chronic otitis externa, tympanic membrane perforation, otomycosis, stenosis, herpes zoster, or myringitis.

8. The method of claim 1, wherein only a single drop of the composition is administered for the duration of treatment.

9. The method of claim 1, wherein the method provides for a sustained linear release rate of the anti-infective agent.

10. The method of claim 1, wherein the anti-infective agent is released for up to 14 days after administration.

11. The method of claim 1, wherein the anesthetic is not encapsulated in a microparticle.

12. The method of claim 1, wherein the anti-infective agent comprises ceftriaxone.

13. The method of claim 1, wherein the anti-infective agent comprises ciprofloxacin.

14. The method of claim 1, wherein the anesthetic is lidocaine.

15. The method of claim 14, wherein the anti-infective agent comprises ciprofloxacin.

16. The method of claim 1, further comprising co-administering an acid for maintaining and/or restoring the pH of the ear canal.

17. The method of claim 1, wherein the anti-infective agent and the anesthetic are simultaneously released for at least partial amount of the time that the composition resides within the ear.

18. The method of claim 1, wherein the composition resides within the ear for at least seven days after administration.

19. The method of claim 1, further comprising removing the composition from the ear within 21 days after administration.

20. The method of claim 19, wherein removing the composition comprises irrigation of the ear with saline.

21. The method of claim 15, wherein the ear condition is acute otitis media.

22. The method of claim 1, wherein the hydrogel comprises a polymer made from N-isopropylacrylamide.

23. The method of claim 1, wherein the polymer microparticles comprise poly (lactic-co-glycolic) acid.

24. The method of claim 1, wherein the hydrogel comprises a polymer made from N-isopropylacrylamide and the polymer microparticles comprise poly (lactic-co-glycolic) acid.

25. A method for treating an ear condition in a subject, comprising topically administering to the ear of the subject in need thereof a composition comprising (i) anti-infective agent-loaded biodegradable polymer microparticles distributed within a thermoresponsive hydrogel; and (ii) an anesthetic distributed within the thermoresponsive hydrogel, wherein the anesthetic is not encapsulated in a microparticle.

26. A method for treating an ear condition in a subject, comprising topically administering to the ear of the subject in need thereof a composition comprising (i) anti-infective agent-loaded biodegradable polymer microparticles distributed within a thermoresponsive hydrogel; and (ii) an anesthetic distributed within the thermoresponsive hydrogel, wherein the anesthetic is lidocaine, benzocaine, or a combination thereof, wherein the hydrogel comprises a polymer made from N-isopropylacrylamide.

27. A method for treating an ear condition in a subject, comprising topically administering to the ear of the subject in need thereof a composition comprising (i) anti-infective agent-loaded biodegradable polymer microparticles distributed within a thermoresponsive hydrogel; and (ii) an anesthetic distributed within the thermoresponsive hydrogel, wherein the anesthetic is lidocaine, benzocaine, or a combination thereof, wherein the polymer microparticles comprise poly (lactic-co-glycolic) acid.

28. The method of claim 25, wherein the anti-infective agent is selected from ofloxacin, ciprofloxacin, finafloxacin, neomycin, gentamicin, tobramycin, tolnaftate, nystatin, clotrimazole, miconazole, or a combination thereof.

29. The method of claim 25, wherein the ear condition is acute otitis media.

30. The method of claim 25, wherein the ear condition is acute or chronic otitis externa, tympanic membrane perforation, otomycosis, stenosis, herpes zoster, or myringitis.

31. The method of claim 25, wherein only a single drop of the composition is administered for the duration of treatment.

32. The method of claim 25, wherein the method provides for a sustained linear release rate of the anti-infective agent.

33. The method of claim 25, wherein the anti-infective agent is released for up to 14 days after administration.

34. The method of claim 25, wherein the anti-infective agent comprises ciprofloxacin.

35. The method of claim 25, wherein the anesthetic is lidocaine.

36. The method of claim 35, wherein the anti-infective agent comprises ciprofloxacin.

* * * * *